(12) United States Patent
Davis et al.

(10) Patent No.: US 8,777,931 B2
(45) Date of Patent: Jul. 15, 2014

(54) RETRACTABLE LUER LOCK FITTINGS (75) Inventors: Sherman George Davis, Laguna Niguel, CA (US); Eric Lee, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 346 days.

(21) Appl. No.: 13/213,519

(22) Filed: Aug. 19, 2011

(65) Prior Publication Data
US 2013/0046287 A1 Feb. 21, 2013

(51) Int. Cl.
*A61M 39/10* (2006.01)

(52) U.S. Cl.
USPC .......................................... 604/533; 285/332

(58) Field of Classification Search
CPC ................ A61M 39/1011; A61M 2039/1033; A61M 2039/1077; A61M 2039/1016
USPC .......... 285/92, 332, 332.1; 604/533, 534, 535
See application file for complete search history.

(56) References Cited

U.S. PATENT DOCUMENTS

| | | | |
|---|---|---|---|
| 2,545,263 A | 3/1951 | Corydon, II | |
| 3,225,435 A | 12/1965 | Anthon | |
| 3,394,954 A | 7/1968 | Sarns | |
| 3,623,484 A | 11/1971 | Schultz | |
| 3,876,234 A | 4/1975 | Harms | |
| D237,552 S | 11/1975 | Willmott et al. | |
| 3,941,127 A | 3/1976 | Froning | |
| 4,046,479 A | 9/1977 | Paley | |
| 4,069,826 A | 1/1978 | Sessions et al. | |
| 4,076,285 A | 2/1978 | Martinez | |
| 4,133,312 A | 1/1979 | Burd | |
| 4,266,815 A | 5/1981 | Cross | |
| 4,294,250 A | 10/1981 | Dennehey | |
| 4,296,949 A | 10/1981 | Muetterties et al. | |
| 4,346,703 A | 8/1982 | Dennehey | |
| 4,346,704 A | 8/1982 | Kulle | |
| 4,360,024 A | 11/1982 | Wallace | |
| 4,369,991 A | 1/1983 | Linder | |

(Continued)

FOREIGN PATENT DOCUMENTS

AU 2007200991 A1 3/2007
EP 0028198 A1 5/1981

(Continued)

OTHER PUBLICATIONS

Lee, Eric, Collar Connector, U.S. Appl. No. 13/273,288, filed Oct. 14, 2011, 24 pages.

(Continued)

*Primary Examiner* — James Hewitt (57) ABSTRACT

The system has a male tubing fitting extending along a longitudinal axis. The male tubing fitting has a first internal bore and an end portion including a male plug. The system also has a female tubing fitting that has a second internal bore configured to receive the male plug. Also, the system has a collar disposed about the male tubing fitting and positioned to slide freely along the longitudinal axis from a first position to a second position. In the first position the male and female tubing fittings are unlocked with respect to each other such that the male plug is removably insertable into the second internal bore of the female tubing fitting. In the second position the male and female fittings are locked with respect to each other such that the male plug is prevented from being removed from the second internal bore of the female tubing fitting.

12 Claims, 6 Drawing Sheets

(56) References Cited

U.S. PATENT DOCUMENTS

| | | |
|---|---|---|
| 4,425,124 A | 1/1984 | Womack |
| 4,439,188 A | 3/1984 | Dennehey et al. |
| 4,451,069 A | 5/1984 | Melone |
| 4,452,473 A | 6/1984 | Ruschke |
| 4,511,359 A | 4/1985 | Vaillancourt |
| 4,538,836 A | 9/1985 | Krutten |
| 4,573,978 A | 3/1986 | Reilly |
| 4,581,012 A | 4/1986 | Brown et al. |
| 4,607,868 A | 8/1986 | Harvey et al. |
| 4,617,012 A | 10/1986 | Vaillancourt |
| 4,639,019 A | 1/1987 | Mittleman |
| 4,642,091 A | 2/1987 | Richmond |
| 4,758,023 A | 7/1988 | Vermillion |
| 4,778,447 A | 10/1988 | Velde et al. |
| 4,785,858 A | 11/1988 | Valentini et al. |
| 4,810,241 A | 3/1989 | Rogers |
| D303,013 S | 8/1989 | Konopka |
| 5,047,021 A | 9/1991 | Utterberg |
| 5,071,413 A | 12/1991 | Utterberg |
| 5,078,699 A | 1/1992 | Haber et al. |
| 5,125,915 A | 6/1992 | Berry et al. |
| 5,135,489 A | 8/1992 | Jepson et al. |
| 5,176,415 A | 1/1993 | Choksi |
| 5,201,717 A | 4/1993 | Wyatt et al. |
| 5,203,775 A | 4/1993 | Frank et al. |
| D339,417 S | 9/1993 | Sampson et al. |
| 5,284,475 A | 2/1994 | Mackal |
| 5,292,308 A | 3/1994 | Ryan |
| 5,310,524 A | 5/1994 | Campbell et al. |
| 5,352,215 A | 10/1994 | Thome et al. |
| 5,356,396 A | 10/1994 | Wyatt et al. |
| 5,413,556 A | 5/1995 | Whittingham |
| 5,425,528 A | 6/1995 | Rains et al. |
| 5,441,487 A | 8/1995 | Vedder |
| D363,542 S | 10/1995 | Parris et al. |
| 5,466,020 A | 11/1995 | Page et al. |
| 5,470,324 A | 11/1995 | Cook et al. |
| 5,578,059 A | 11/1996 | Patzer |
| 5,582,600 A | 12/1996 | Loh |
| 5,607,392 A | 3/1997 | Kanner |
| 5,609,584 A | 3/1997 | Gettig et al. |
| 5,611,785 A | 3/1997 | Mito et al. |
| 5,620,427 A | 4/1997 | Werschmidt et al. |
| 5,630,427 A | 5/1997 | Hastings |
| 5,651,776 A | 7/1997 | Appling et al. |
| 5,697,898 A | 12/1997 | Devine |
| 5,702,374 A | 12/1997 | Johnson |
| 5,775,744 A | 7/1998 | Smith, III |
| 5,797,889 A | 8/1998 | Steinman |
| 5,830,189 A | 11/1998 | Chang |
| 5,855,568 A | 1/1999 | Battiato et al. |
| 6,086,762 A | 7/2000 | Guala |
| 6,096,022 A | 8/2000 | Layman et al. |
| 6,152,913 A | 11/2000 | Feith et al. |
| D435,652 S | 12/2000 | Nazarifar et al. |
| 6,156,025 A | 12/2000 | Niedospial et al. |
| 6,183,464 B1 | 2/2001 | Sharp et al. |
| 6,224,588 B1 | 5/2001 | Jentzen |
| 6,290,676 B1 | 9/2001 | Bierman |
| 6,332,633 B1 | 12/2001 | Fitoussi |
| D454,637 S | 3/2002 | Nestenborg |
| 6,361,687 B1 | 3/2002 | Ford et al. |
| 6,402,207 B1 | 6/2002 | Segal et al. |
| D462,759 S | 9/2002 | Sutton et al. |
| 6,460,592 B1 | 10/2002 | Sano et al. |
| 6,463,979 B1 | 10/2002 | Sano et al. |
| 6,485,483 B1 | 11/2002 | Fujii |
| 6,562,023 B1 | 5/2003 | Marrs et al. |
| 6,585,683 B2 | 7/2003 | Sutton et al. |
| 6,595,964 B2 | 7/2003 | Finley et al. |
| 6,612,624 B1 | 9/2003 | Segal et al. |
| D483,869 S | 12/2003 | Tran et al. |
| 6,673,059 B2 | 1/2004 | Guala |
| 6,843,513 B2 | 1/2005 | Guala |
| 6,893,056 B2 | 5/2005 | Guala |
| 6,955,669 B2 | 10/2005 | Curutcharry |
| 7,083,605 B2 | 8/2006 | Miyahara |
| 7,137,654 B2 | 11/2006 | Segal et al. |
| 7,316,679 B2 | 1/2008 | Bierman |
| 7,472,932 B2 | 1/2009 | Weber et al. |
| 7,497,484 B2 | 3/2009 | Ziman |
| 7,523,967 B2 | 4/2009 | Steppe |
| 7,658,420 B2 | 2/2010 | Harger et al. |
| 7,998,134 B2 | 8/2011 | Fangrow et al. |
| 8,043,280 B2 | 10/2011 | Bierman |
| 8,057,095 B2 | 11/2011 | Wendler |
| 8,192,421 B2 | 6/2012 | Lopez et al. |
| 2002/0038114 A1 | 3/2002 | Segura |
| 2002/0099360 A1 | 7/2002 | Bierman |
| 2002/0123739 A1 | 9/2002 | Haack et al. |
| 2002/0174956 A1 | 11/2002 | Sano et al. |
| 2003/0158539 A1 | 8/2003 | Bouphavichith et al. |
| 2003/0195539 A1 | 10/2003 | Attinger et al. |
| 2004/0039351 A1 | 2/2004 | Barrett |
| 2004/0201216 A1 | 10/2004 | Segal et al. |
| 2004/0260243 A1 | 12/2004 | Rickerd |
| 2005/0010157 A1 | 1/2005 | Baraldi et al. |
| 2005/0016620 A1 | 1/2005 | Proulx et al. |
| 2005/0101939 A1 | 5/2005 | Mitchell |
| 2005/0107770 A1 | 5/2005 | Schweikert et al. |
| 2005/0251102 A1* | 11/2005 | Hegland et al. ............... 604/500 |
| 2005/0265877 A1 | 12/2005 | Robert |
| 2006/0015086 A1 | 1/2006 | Rasmussen et al. |
| 2006/0047251 A1 | 3/2006 | Bickford Smith et al. |
| 2006/0076772 A1 | 4/2006 | Zimmerman |
| 2006/0079832 A1 | 4/2006 | Akahoshi |
| 2006/0293640 A1 | 12/2006 | Greco |
| 2007/0032776 A1 | 2/2007 | Skinner et al. |
| 2007/0043334 A1 | 2/2007 | Guala |
| 2007/0088327 A1 | 4/2007 | Guala |
| 2007/0156117 A1 | 7/2007 | Adams et al. |
| 2007/0161946 A1 | 7/2007 | Cerasoli |
| 2007/0218757 A1 | 9/2007 | Guala |
| 2007/0219483 A1 | 9/2007 | Kitani et al. |
| 2007/0224865 A1 | 9/2007 | Fangrow |
| 2007/0225684 A1 | 9/2007 | Wentling et al. |
| 2007/0282278 A1 | 12/2007 | Knight |
| 2008/0004600 A1 | 1/2008 | Kitani et al. |
| 2008/0063467 A1 | 3/2008 | Ferrari |
| 2008/0077118 A1 | 3/2008 | Bierman |
| 2008/0097409 A1 | 4/2008 | Stephens |
| 2008/0100061 A1 | 5/2008 | Sage et al. |
| 2008/0103456 A1 | 5/2008 | Johnson et al. |
| 2008/0114314 A1 | 5/2008 | Muehlhoff et al. |
| 2008/0172068 A1 | 7/2008 | Adams et al. |
| 2008/0303267 A1 | 12/2008 | Schnell et al. |
| 2009/0036764 A1 | 2/2009 | Rivas et al. |
| 2009/0062776 A1 | 3/2009 | Funamura et al. |
| 2009/0069792 A1 | 3/2009 | Frey et al. |
| 2009/0216206 A1 | 8/2009 | Nishtala et al. |
| 2012/0046649 A1 | 2/2012 | Bierman |

FOREIGN PATENT DOCUMENTS

| | | |
|---|---|---|
| EP | 0015897 B1 | 7/1983 |
| EP | 0143517 A1 | 6/1985 |
| EP | 0349745 A1 | 1/1990 |
| EP | 0411521 A1 | 2/1991 |
| EP | 0987046 A1 | 3/2000 |
| EP | 1867359 A2 | 12/2007 |
| EP | 1872824 A1 | 1/2008 |
| EP | 1955685 A1 | 8/2008 |
| EP | 2095841 A1 | 9/2009 |
| EP | 1551475 B1 | 12/2011 |
| GB | 2146405 A | 4/1985 |
| GB | 2383828 A | 7/2003 |
| WO | WO 90/12606 A2 | 11/1990 |
| WO | WO 90/12606 A3 | 10/1992 |
| WO | WO 95/04570 A1 | 2/1995 |
| WO | WO 95/15194 A1 | 6/1995 |
| WO | WO 03/103746 A1 | 12/2003 |
| WO | WO 2005/110200 A1 | 11/2005 |
| WO | WO 2007/003281 A1 | 1/2007 |
| WO | WO 2007/015831 A1 | 2/2007 |

(56) References Cited

FOREIGN PATENT DOCUMENTS

| WO | WO 2007/089309 A2 | 5/2007 |
|----|----|----|
| WO | WO 2009/010998 A1 | 1/2009 |
| WO | WO 2009/024807 A1 | 2/2009 |
| WO | WO 2009/044364 A2 | 4/2009 |
| WO | WO 2007/089309 A3 | 5/2009 |
| WO | WO 2009/044364 A3 | 5/2009 |
| WO | WO 2009/076717 A1 | 6/2009 |
| WO | WO 2009/095760 A1 | 8/2009 |
| WO | 2013/028273 A1 | 2/2013 |

OTHER PUBLICATIONS

Prosecution History of US Patent No. 7,523,967, filed Oct. 26, 2005, 72 pages.
British Standard EN 20594-1:1994 ISO 594-1:1986; "Conical fittings with a 6% (Luer)taper for syringes, needles and certain other medical equipment—Part 1 General Requirements"—Including Amendment A1:1997; 1998; 17 pages; British Standards Institution.
British Standard EN 1707:1997; "Conical fittings with a 6% (Luer) taper for syringes, needles and certain other medical equipment—Lock fittings"; 1997; 21 pages; British Standards Institution.
International Searching Authority, International Search Report, PCT/US2012/046158, Sep. 17, 2012, 2 pages.
International Searching Authority, Written Opinion of the International Searching Authority, PCT/US2012/046158, Sep. 17, 2012, 7 pages.
http://www.bbraunusa.com/index.cfm?uuid=56964CC0D0B759A1E360264300989ADD, Dec. 1, 2009, 1 page.
Internet Search Document from Colder Products Company's website; "SMC and SMF1 Series"; Copyright Colder Products 2002-2005; 1 page.
Internet Search Document from Colder Products Company's website: "Medical Products Overview"; Copyright Colder Products 2002-2005; 6 pages.

* cited by examiner

RETRACTABLE LUER LOCK FITTINGS

BACKGROUND OF THE INVENTION

The present disclosure relates generally to a retractable luer lock fitting configured to couple tubings to a surgical instrument used in ophthalmic surgeries.

A variety of surgical systems are used in ophthalmic surgery. For example, such systems may include a surgical console, accessories (e.g. footswitch, reusable handpieces), and various consumables. The consumables typically include tubing sets that connect to the console and provide a pathway from the console in the non-sterile field to a surgical instrument or other device that is used in and remains in the sterile field. A tubing fitting is typically used to fluidly couple tubing from the console to a surgical device.

Luer fittings are used extensively on medical devices such as syringes, needles, catheters, and tubing sets. Two types are common: luer slip fittings and luer lock fittings. Both types consist of a male fitting and a female fitting. Luer slip fittings are sealably engaged by a friction fit between the male and female luer surfaces. Luer lock fittings are sealably engaged with an additional lock feature on the male and female luer surfaces. More specifically, the external female surface includes a pair of opposed flanges proximate its opening. The male fitting includes a collar that receives the female fitting and has a single internal spiral thread that rotationally engages the opposed flanges to sealably engage with respect to each other.

As ophthalmic surgery continues to increase in sophistication and complexity, the need remains for new tubing fittings that will prevent the accidental misconnection of a standard luer slip fitting and/or a standard luer lock fitting. Additionally, there remains a need to simplify the connection between male and female tubing. Furthermore, there remains a need for such a connection to be backwards compatible with existing accessories with no locking features.

The systems, devices, and methods disclosed herein overcome at least one of the shortcomings in the prior art.

SUMMARY OF THE INVENTION

In one exemplary aspect, the present disclosure is directed to a system. The system has a male tubing fitting extending along a longitudinal axis. The male tubing fitting has a first internal bore and an end portion including a male plug. The system also has a female tubing fitting that has a second internal bore configured to receive the male plug. Also, the system has a collar disposed about the male tubing fitting and positioned to slide freely along the longitudinal axis from a first position to a second position. In the first position the male and female tubing fittings are unlocked with respect to each other such that the male plug is removably insertable into the second internal bore of the female tubing fitting. In the second position the male and female fittings are locked with respect to each other such that the male plug is prevented from being removed from the second internal bore of the female tubing fitting.

In one exemplary aspect, the present disclosure is directed to a system. The system has a male tubing fitting having an exterior surface extending along a longitudinal axis and a tapered end portion. The male tubing fitting includes a first internal bore. The system also has a female tubing fitting that has a second internal bore configured to receive the tapered end portion. The female tubing fitting has an exterior surface that includes a projection. Also, the system has a collar disposed about the exterior surface of the male tubing and rotatable about the longitudinal axis with respect to the male tubing fitting. The collar includes a threaded internal bore that has an interior surface that includes a thread pattern defining a space configured to removably receive the projection of the female tubing fitting. Rotation of the collar about the longitudinal axis relative to the male tubing fitting when the projection is positioned within the space sealingly engages and locks the first internal bore of the male tubing fitting with the second internal bore of the female tubing fitting.

In one exemplary aspect, the present disclosure is directed to a system. The system has a male tubing fitting that has an exterior surface extending along a longitudinal axis and includes a retention member. The male tubing further includes a first internal bore and a tapered end portion. Also, the system has a female tubing fitting that has a second internal bore configured to receive the tapered end portion. Additionally, the system has a collar disposed about the exterior surface of the male tubing fitting and selectively retained by the retention member at a first position along the longitudinal axis. The collar includes an elastically deformable portion that deforms in order to position the collar beyond the selective retainment of the retention member to a second position along the longitudinal axis. In the first position the male and female tubing fittings are unlocked with respect to each other such that the tapered end portion is removably insertable into the second internal bore of the female tubing fitting. In the second position the male and female fittings are locked with respect to each other such that the tapered end portion is prevented from being removed from the second internal bore of the female tubing fitting.

These and other aspects, forms, objects, features, and benefits of the present disclosure will become apparent from the following detailed drawings and description.

BRIEF DESCRIPTION OF THE DRAWINGS

The accompanying drawings, which are incorporated in and constitute a part of the specification, illustrate embodiments of the present disclosure. Together with a general description of the present disclosure given above, and the detailed description given below, the drawings serve to exemplify the embodiments of the present disclosure.

DETAILED DESCRIPTION OF THE INVENTION

The present disclosure relates generally to the field of ophthalmic surgery, and more particularly to a retractable luer lock fitting configured to couple tubings to a surgical instrument used in ophthalmic surgeries. For the purposes of promoting an understanding of the principles of the present disclosure, reference will now be made to embodiments or examples illustrated in the drawings, and specific language will be used to describe these examples. It will nevertheless be understood that no limitation of the scope of the present disclosure is thereby intended. Any alteration and further modifications in the described embodiments, and any further applications of the principles of the present disclosure as described herein are contemplated as would normally occur to one skilled in the art to which the disclosure relates.

Figures 1, 2:
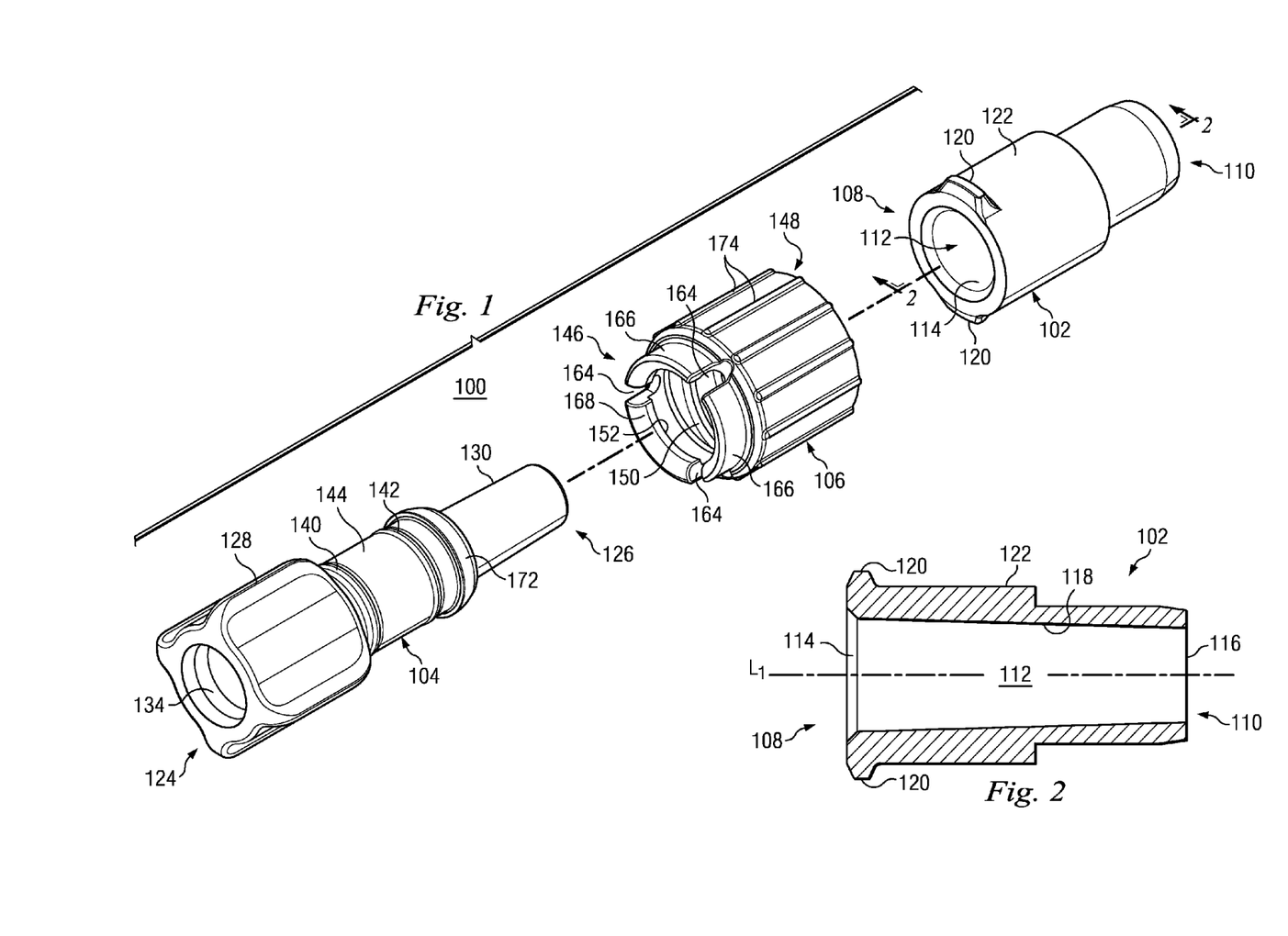
FIG. 1 is an illustration of an exploded view of an exemplary retractable luer lock system according to one aspect of the present disclosure.
FIG. 2 is an illustration of a cross-sectional view of a female tubing fitting used in the retractable luer lock system shown in FIG. 1 according to one aspect of the present disclosure.

FIG. 1 is an illustration of an exploded view of an exemplary retractable luer lock system 100. As shown, retractable luer lock system 100 includes female tubing fitting 102, or female luer lock. Additionally, retractable luer lock system 100 includes male tubing fitting 104, or male luer fitting. Also, retractable luer lock system 100 includes retractable locking collar 106. As will be described in greater detail below, retractable locking collar 106 is configured to retract, translate, slide, move, and/or rotate about male tubing fitting 104. As such, retractable locking collar 106 can move axially with respect to male tubing fitting 104 to effectively lock and unlock the male tubing fitting 104 and female tubing fitting 102 together.

Referring to FIGS. 1 and 2, female tubing fitting 102 is shown having a generally tubular shape extending from a proximal end 108 to a distal end 110. An internal bore 112 extends through female tubing fitting 102. Proximal opening 114 is in communication with the internal bore 112 at the proximal end 108 and distal opening 116 is in communication with the internal bore 112 at the distal end 110. As shown, internal bore 112 is defined by interior surface 118 which continuously tapers from the proximal end 108 to the distal end 110. As such, internal bore 112 has a luer taper.

At the proximal end 108, female tubing fitting 102 includes projections 120, or wings extending from external surface 122. Here, female tubing fitting 102 has a pair of opposing projections 120 that are positioned on opposing sides of the proximal end 108. Projections 120 extend substantially transverse to longitudinal axis $L_1$ of the female tubing fitting 102. Moreover, each projection 102 extends in opposing directions from longitudinal axis $L_1$. Although shown as two projections 120, it is contemplated in other embodiments that female tubing fitting 102 has one or more than two projections 120. As will be described in greater detail below, projections 120 assist in locking the female tubing fitting 102 to the male tubing fitting 104.

Figure 3:
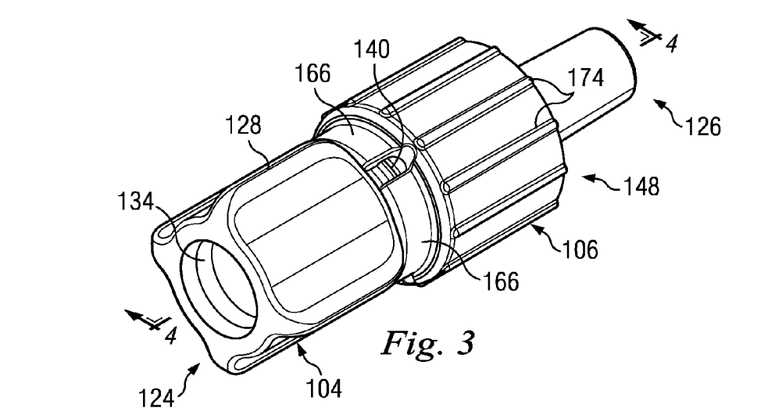
FIG. 3 is an illustration of a perspective view of a male tubing fitting including a retractable locking collar used in the retractable luer lock system shown in FIG. 1 according to one aspect of the present disclosure.
Figure 4:
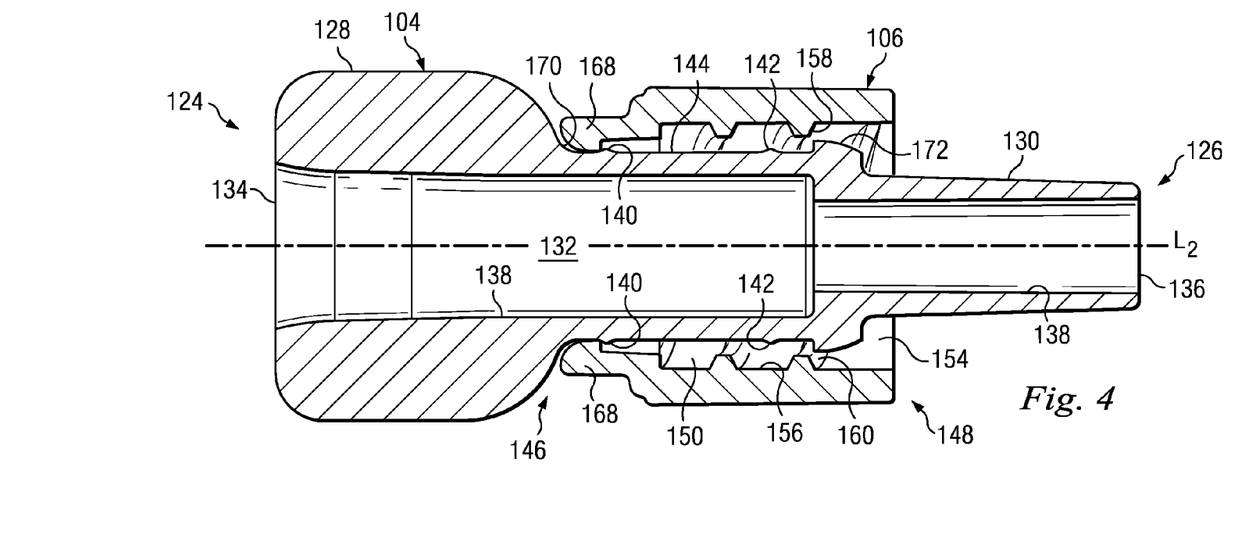
FIG. 4 is an illustration of a cross-sectional view of the male tubing fitting including the retractable locking collar shown in FIG. 3 according to one aspect of the present disclosure.

Referring to FIGS. 1, 3, and 4, male tubing fitting 104 extends from a proximal end 124 to a distal end 126. The proximal end 124 includes flanges 128 and distal end 126 forms a male plug 130, or tapered distal end portion. In that regard, flanges 128 provide a traction or gripping surface for a user of system 100 to use while connecting and/or disconnecting female and male tubing fittings 102 and 104. Moreover, male plug 130 has a luer taper and is sized and shaped to be received within internal bore 112 of female tubing fitting 102. Thus, flanges 128 allow a user to grip male tubing fitting 104 during insertion of or removal of male plug 130 into or from internal bore 112 of female tubing fitting 102. As such, flanges 128 assist in ease of connection and disconnection between female and male tubing fittings 102 and 104.

As shown, male tubing fitting 104 includes an internal bore 132 extending through male tubing fitting 104. Proximal opening 134 is in communication with the internal bore 132 at the proximal end 124 and distal opening 136 is in communication with the internal bore 132 at the distal end 126. Internal bore 132 is defined by interior surface 138. In that regard, interior surface 138 tapers and/or steps down from the proximal end 124 to the distal end 126. As such, the diameter of internal bore 132 at the proximal end 124 of male tubing fitting 104 is greater than the diameter of internal bore at the distal end 126 of male tubing fitting 104.

As best shown in FIGS. 1 and 4, male tubing fitting 104 includes a proximal retention member 140, or annular nub, and a distal retention member 142, or annular nub. Proximal and distal retention members 140 and 142, extend around the perimeter of male tubing fitting 104 forming a raised annular ring, portion, and/or ridge along exterior surface 144 of male tubing fitting 104. As will be described in greater detail below, proximal and distal retention members 140 and 142 interact with retractable locking collar 106 in order to selectively retain and/or hold the locking collar in a desired position along exterior surface 144 of male tubing fitting 104.

Referring to FIGS. 1, 3, and 4 retractable locking collar 106 extends from a proximal end 146 to a distal end 148. As shown, an internal bore 150 extends through retractable locking collar 106. Proximal opening 152 is in communication with the internal bore 150 at the proximal end 146 and distal opening 154 is in communication with the internal bore 150 at the distal end 148.

Figure 5:
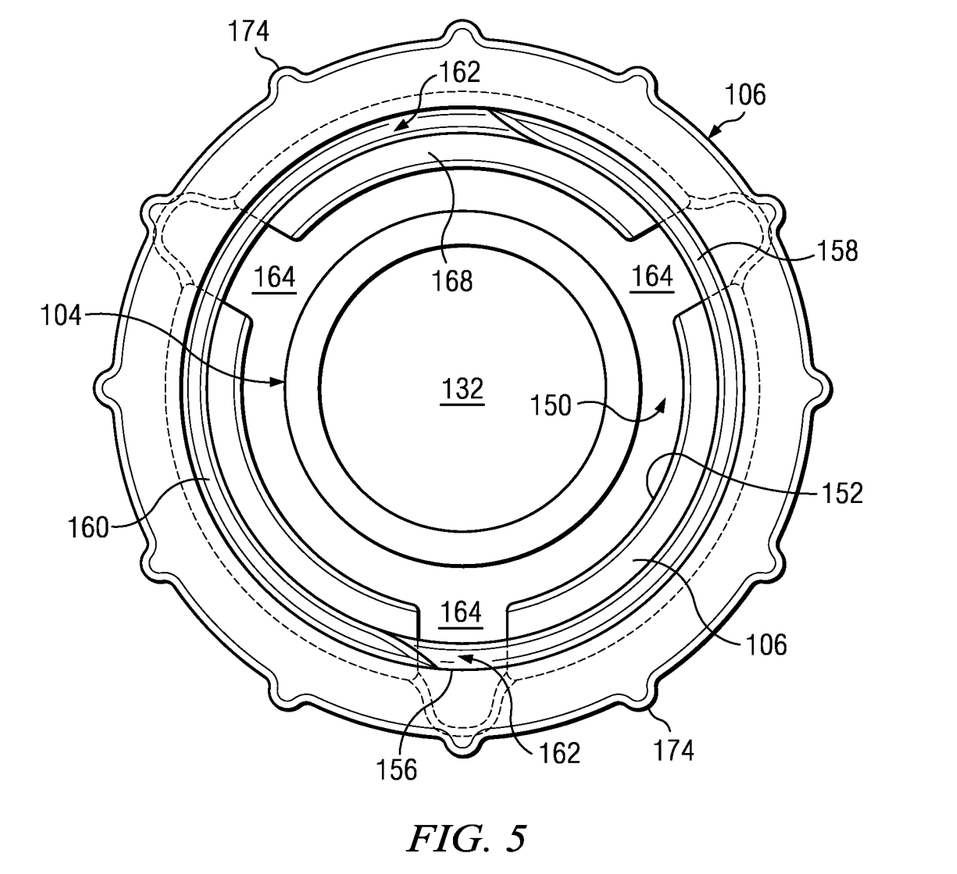
FIG. 5 is an illustration of an end view of the male tubing fitting including the retractable locking collar shown in FIG. 3 according to one aspect of the present disclosure.

Internal bore 150 is defined by interior surface 156. As best shown in FIG. 5, interior surface 156 includes threads 158 and 160, or sloping ramps. Threads 158 and 160 form a double helix thread pattern within internal bore 150. In that regard, threads 158 and 160 are sloped in opposite directions as the threads extend circumferentially about interior surface 156. Additionally, threads 158 and 160 form a pair of opposing spaces 162 configured for removably receiving projections 120 of female tubing fitting 102. As will be described in greater detail below, when projections 120 are placed in spaces 162 and retractable locking collar 106 is rotated in a first direction about male tubing fitting 104, male tubing fitting 104 is sealingly engaged with and locked into female tubing fitting 102.

As shown, proximal end 146 of retractable locking collar 106 includes relief portions 164, or apertures, or slits. In that regard, exterior surface 166 of retractable locking collar 106 is interrupted by relief portions 164. Relief portions 164 extend from the exterior surface 166 through to the interior surface 156 defining internal bore 150. As such, relief portions 164 increase the flexibility and/or elasticity of proximal end 146. Thus, proximal end 146 is elastically deformable because of relief portions 164.

Proximal end 146 of retractable locking collar 106 also includes a tapered lip 168 or flange extending into internal bore 150. In that regard, tapered lip 168 is adjacent to and surrounds proximal opening 152. Moreover, tapered lip 168 is interrupted by relief portions 164. As such, tapered lip 168 forms an non-continuous annular lip around proximal opening 152. As described in greater detail below, tapered lip 168 interfaces with proximal and distal retention members 140 and 142 to retain and/or hold the retractable locking collar in a predetermined position along exterior surface 144 of male tubing fitting 104.

Referring to FIGS. 3 and 4, retractable locking collar 106 is disposed around exterior surface 144 of male tubing fitting 104. Retractable locking collar 106 is configured to be positioned along exterior surface 144 of male tubing fitting 104. In that regard, retractable locking collar 106 can retract, translate, slide, move, and/or rotate freely about longitudinal axis $L_2$ of male tubing fitting 104 as the collar moves along exterior surface 144. For example, retractable locking collar 106 is positionable along any portion of exterior surface 144 of male tubing fitting 104 from about base 170 of flanges 128 to ridge 172 of male plug 130.

As best seen in FIGS. 1 and 3, retractable locking collar 106 has a plurality of ridges 174 extending about exterior surface 164. In that regard, ridges 174 provide a gripping surface that enables a user to hold or grasp on to while positioning retractable collar 106 about male tubing fitting 104. Specifically, ridges 174 provide a surface to hold onto while retracting, translating, sliding, moving and/or rotating retractable locking collar 106 about male tubing fitting 104.

Moreover, FIG. 4 shows the retractable locking collar 106 being retained by proximal retention member 140. In this position, retractable locking collar is considered in a retracted position, or first position. As shown, tapered lip 168 of retractable locking collar 106 is positioned between base 170 of flanges 128 and proximal retention member 140 while in the retracted position. Additionally, in the retracted position the proximal retention member 140 abuts the tapered lip 168 of the retracted locking collar thereby selectively retaining the locking collar from moving along exterior surface 144 towards the male plug 130. Thus, in the retracted position, male plug 130 of male tubing fitting 104 is more easily accessible because the locking collar is selectively retained and/or prevented from sliding towards the plug thereby keeping the collar from interfering with use of the plug.

Figure 6:
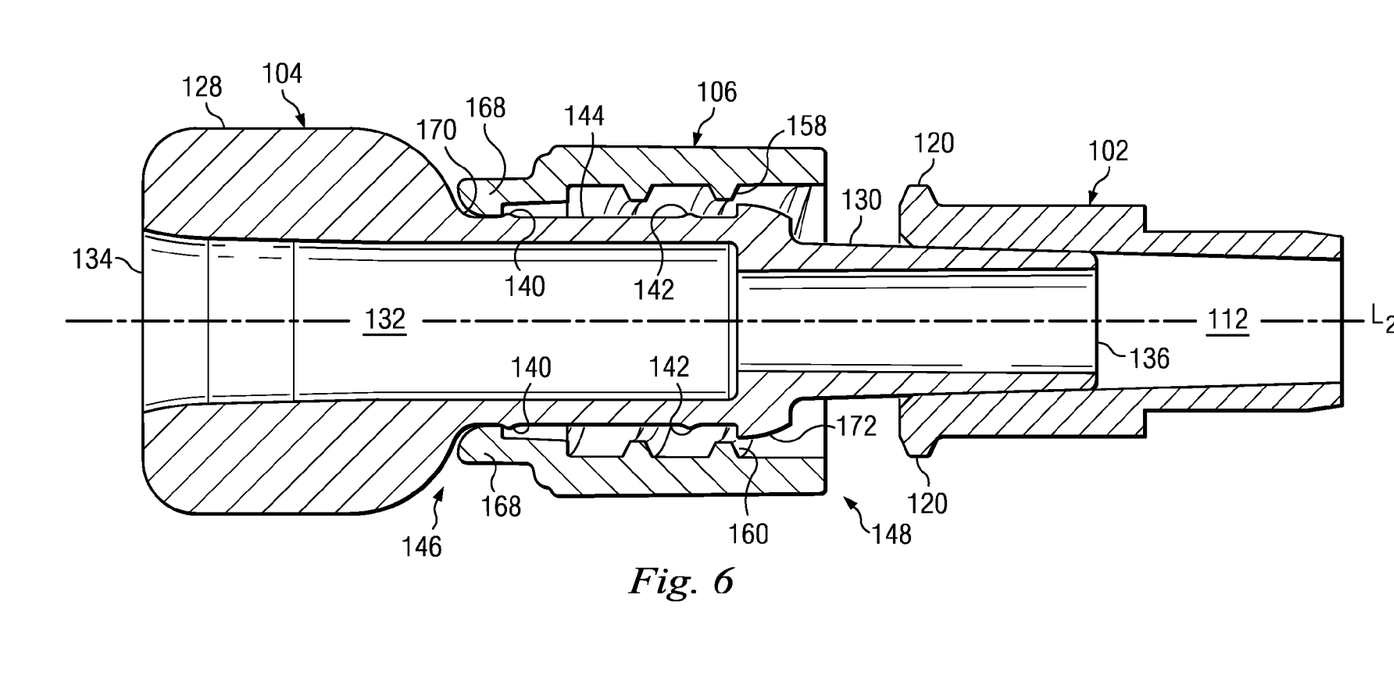
FIG. 6 is an illustration of a cross-sectional view of the exemplary retractable luer lock system of FIG. 1 in an unlocked configuration according to one aspect of the present disclosure.

FIG. 6 shows a cross-sectional view of luer lock system 100 in an unlocked configuration. In the unlocked configuration, retractable locking collar 106 is selectively retained by the proximal retention member 140 in the retracted position. In the retracted position, tapered lip 168 abuts the proximal retention member 140 thereby selectively preventing the locking collar from moving along exterior surface 144 towards the male plug 130. Thus, in the retracted position, male plug 130 of male tubing fitting 104 is more easily accessible because the locking collar is selectively retained and/or prevented from sliding towards the plug thereby keeping the collar from interfering with use of the plug.

As shown in FIG. 6, male plug 130 has been inserted into internal bore 112 of female tubing fitting 102 through proximal opening 114. As discussed above, because retractable locking collar 106 is in the retracted position, the locking collar is selectively retained and/or prevented from sliding towards the plug thereby keeping the collar from interfering with insertion of the plug into the female tubing fitting 102. Moreover, retractable locking collar 106 does not lock the female and male tubing fittings 102 and 104 together when in the retracted position. Thus, while the retractable locking collar 106 is in the retracted position male plug 130 is removably insertable within internal bore 112 of female tubing fitting 102. In other words, male plug 130 can be inserted into and removed from internal bore 112 of female tubing fitting 102 when the retractable locking collar 106 is in the retracted position. Accordingly, in the unlocked configuration retractable locking collar 106 is retracted and not locking the female and male tubing fittings 102 and 104 together.

Moreover, flanges 128 further assist during connection of male tubing fitting 104 and female tubing fitting 102. In that regard, flanges 128 of male tubing fitting 104 enable a user to more easily grip male tubing fitting 104 during insertion of male plug 130 into internal bore 112. For example, flanges 128 provide a grip surface that allows a user to twist, push, pull, and/or the like on male tubing fitting 104 during connection of female and male tubing fittings 102 and 104. Accordingly, in the unlocked configuration flanges 128 help position the male tubing fitting 104 within the female tubing fitting 102.

Figure 7:
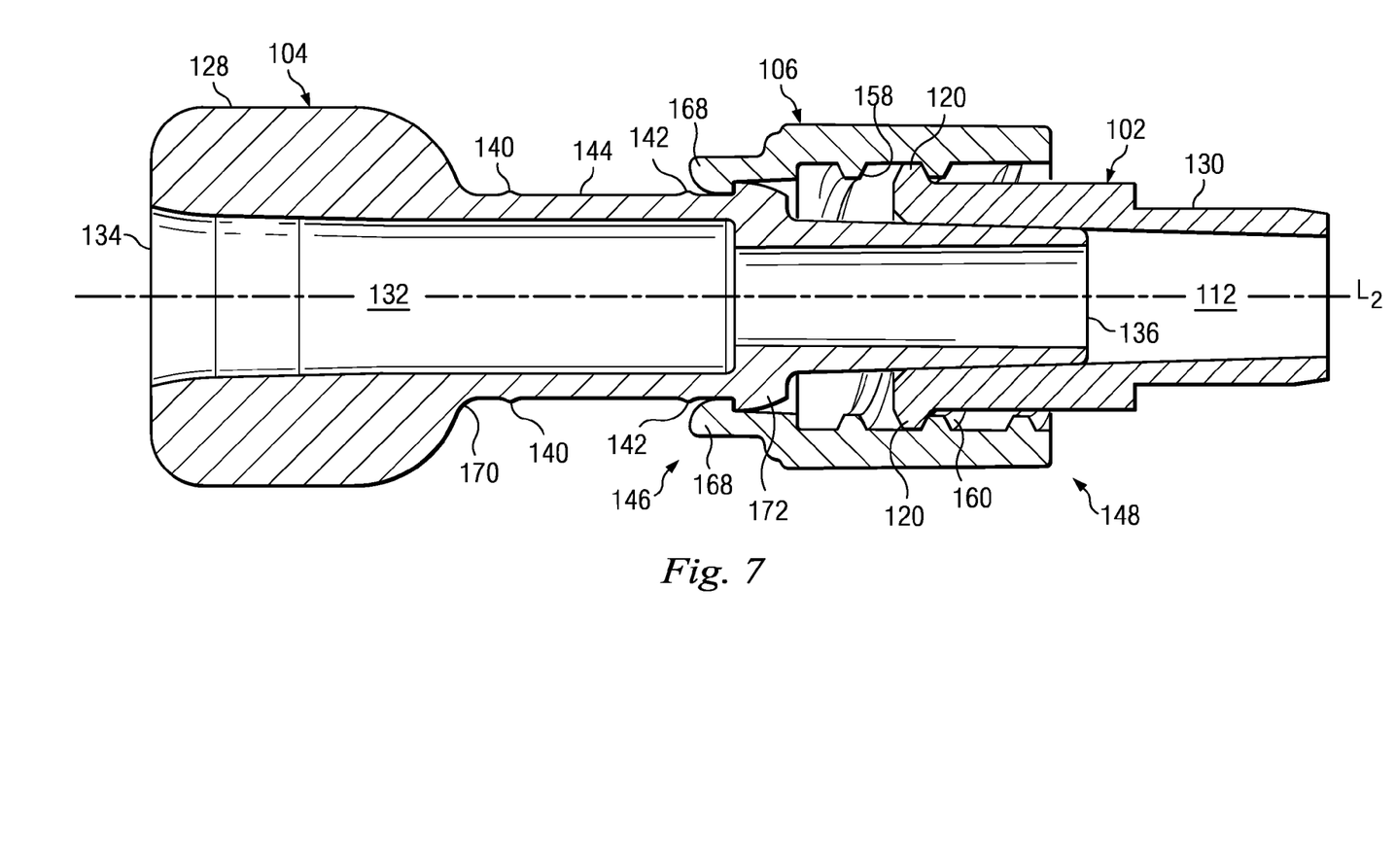
FIG. 7 is an illustration of a cross-sectional view of the exemplary retractable luer lock system of FIG. 1 in a locked configuration according to one aspect of the present disclosure.

FIG. 7 shows a cross-sectional view of luer lock system 100 in a locked configuration. From the unlocked configuration shown in FIG. 6, retractable locking collar 106 has moved along exterior surface 144 and is now retained by distal retention member 142 in an non-retracted position, or second position. As shown, tapered lip 168 of retractable locking collar 106 is positioned between distal retention member 142 and ridge 172 of male plug 130 while in the non-retracted position.

To achieve the non-retracted position, retractable locking collar 106 has been moved in a first direction along longitudinal axis $L_2$ towards male plug 130. In that regard, because the proximal end 146 has increased flexibility because of relief portions 164, the proximal end 146 can deform or flex outwardly away from exterior surface 144 when passing over and beyond proximal and distal retention member 140 and 142, respectively, as it moves along exterior surface 144 towards male plug 130. Specifically, when sufficient force is applied to locking collar in the direction of male plug 130, the tapered lip 168 flexes outwardly away from exterior surface 144 when the lip abuts against proximal and distal retention members 140 and 142, respectively. As such the tapered lip 168 is able to pass over the proximal and distal retention members 140 and 142, respectively, and move along exterior surface 144 towards male plug 130 into the non-retracted configuration. Accordingly, in the non-retracted configuration tapered lip 168 abuts against distal retention member 142 and thereby selectively retains the locking collar from moving along exterior surface 144 in an opposing second direction along longitudinal axis $L_2$ towards the flanges 128.

Additionally, FIG. 7 shows that male tubing fitting 104 is locked together to female tubing fitting 102 via retractable locking collar 106. In that regard, retractable locking collar 106 has been aligned with respect to projections 120 such that the projections 120 are inserted into spaces 162 of the collar. Moreover, retractable locking collar 106 has been rotated about longitudinal axis $L_2$ in a first direction (e.g. clockwise) to sealingly engage and lock male tubing fitting 104 and female tubing fitting 102 together. As such, internal bore 112 of the female tubing fitting and internal bore 132 of the male tubing fitting 104 are fluidly coupled. Thus, while the retractable locking collar 106 is in the non-retracted position male plug 130 is prevented from being removed from internal bore 112 of female tubing fitting 102. Accordingly, in the locked configuration the retractable locking collar 106 locks the female and male tubing fittings 102 and 104 together to thereby sealingly engage the internal bores of the respective tubings.

It should be noted that in alternative embodiments, retractable locking collar 106 is configured such that it is rotated about longitudinal axis $L_2$ in another direction (e.g. counter-clockwise) to sealingly engage and lock male tubing fitting 104 and female tubing fitting 102 together. In such an alternative embodiment, threads 158 and 160 of retractable locking collar 106 are oriented such that counter-clockwise rotation of retractable locking collar 106 about longitudinal axis $L_2$ sealingly engages and locks male tubing fitting 104 and female tubing fitting 102 together.

Moreover, it should be noted that the locking of male tubing fitting 104 to female tubing 102 via retractable locking collar 106 can occur without rotation or twisting of the tubing fittings. As discussed above, retractable locking collar 106 rotates about longitudinal axis $L_2$ in the first direction relative to male tubing fitting 104 to lock the female and male tubing fittings 102 and 104. However, during this locking process female and male tubing fittings 102 and 104 do not necessarily need to be rotated with respect to each other. As a result, the locking of male and female tubings together is simplified due to the lack of twisting and/or rotation required as result of retractable locking collar 106 locking the tubings together.

Additionally, retractable luer lock system 100 can return to the unlocked configuration shown in FIG. 6 from the locked configuration shown in FIG. 7. In that regard, male tubing fitting 104 and female tubing fitting 102 may be unlocked from each other by rotating retractable locking collar 106 about longitudinal axis $L_2$ in a second direction (e.g. counter-clockwise) relative to male tubing fitting 104. Moreover, from the locked configuration shown in FIG. 7, retractable locking collar 106 is moved along exterior surface 144 such that tapered lip 168 is selectively retained by proximal retention member 140 in the retracted configuration (See FIG. 6). Because the proximal end 146 has increased flexibility as a result of relief portions 164, the proximal end 146 can flex or deform outwardly away from exterior surface 144 (i.e. longitudinal axis $L_2$) when passing over or beyond distal and proximal retention members 142 and 140, respectively, as it moves along exterior surface 144 in a second direction along longitudinal axis $L_2$ towards flanges 128. Specifically, when sufficient force is applied to retractable locking collar 106 in the second direction towards flanges 128, the tapered lip 168 deforms or flexes outwardly away from exterior surface 144 when the lip abuts against distal and proximal retention members 142 and 140, respectively. As such the tapered lip 168 is able to pass beyond the selective retainment of distal and proximal retention members 142 and 140, respectively, and move along exterior surface 144 towards flanges 128 until the retractable locking collar assumes the retracted position.

The following describes an exemplary use of retractable luer lock system 100 in which a healthcare provider uses retractable luer lock system 100 to fluidly couple a surgical instrument to a surgical console. Female tubing fitting 102 is fluidly coupled at distal end 110 to the surgical instrument. As such, internal bore 112 of female tubing fitting 102 is in fluid communication with the surgical instrument.

Male tubing fitting 104 is fluidly coupled to a first end of a piece of conventional plastic tubing. Specifically, the first end of the piece of tubing is inserted into internal bore 132 of the male tubing fitting 104 through proximal opening 134. The opposite end of the piece of plastic tubing is fluidly coupled to the surgical console.

The surgical instrument is then fluidly coupled to the surgical console. In that regard, male plug 130 in inserted into internal bore 112 of female tubing fitting 102. More specifically, the retractable locking collar 106 is in the retracted position during the insertion of male plug 130 into internal bore 122. Then, retractable locking collar 106 is slid along exterior surface 144 of male tubing fitting 104 from the retracted position to the non-retracted position. Additionally, the spaces 162 of retractable locking collar 106 are aligned with respect to projections 120 of female tubing fitting 102. Once the collar is in the non-retracted position and the projections are positioned within spaces 162, the retractable locking collar 106 is rotated in a first direction (e.g. clockwise) about longitudinal axis $L_2$ of male tubing fitting 104. Such rotation sealingly locks male tubing fitting 104 and female tubing fitting 102 together. Accordingly, retractable luer lock system 100 provides a retractable luer lock than enables male and female tubing fittings to be sealingly engaged with respect to each other.

Additionally, male tubing fitting 104 and female tubing fitting 102 may be unlocked by rotating retractable locking collar 106 in a second direction (e.g. counter-clockwise) about longitudinal axis $L_2$ of male tubing fitting 104 that opposes the first direction. Moreover, once unlocked the retractable locking collar is slid along the exterior surface to the retracted position. In the retracted position, the retractable locking collar is no longer locking the female and male tubing fittings 102 and 104 together. As such, flanges 128 are used to provide a gripping surface to assist in pulling, twisting, and/or physically removing the male tubing fitting 104 from the female tubing fitting 102. In other words, with the retractable locking collar 106 in the retracted position, male plug 130 can be removed from internal bore 112 thereby physically disconnecting the female and male tubing fittings 102 and 104 from each other.

Figure 8:
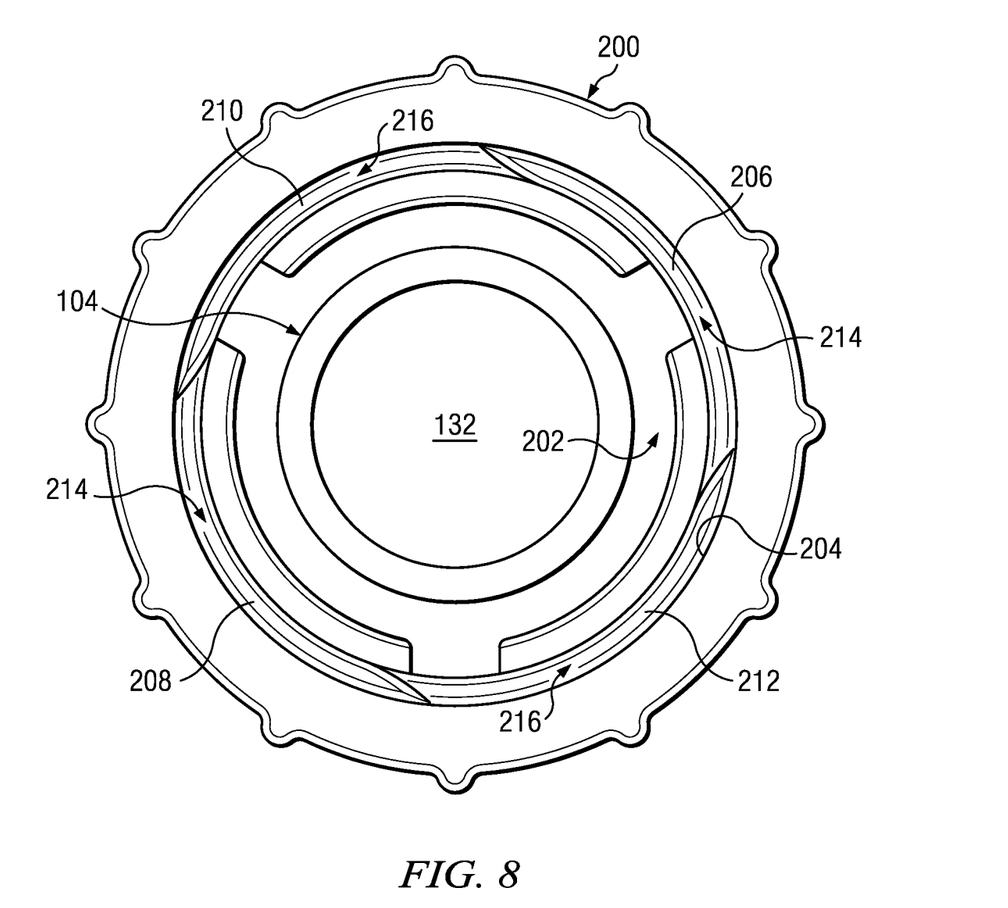
FIG. 8 is an illustration of an end view of the male tubing fitting of FIG. 3 including an alternative retractable locking collar according to one aspect of the present disclosure.

FIG. 8 shows an end view of an alternative retractable locking collar 200 according to one aspect of the present disclosure. Retractable locking collar 200 is similar to retractable locking collar 106. Moreover, locking collar 200 can be used in place of locking collar 106 in retractable luer lock system 100. Moreover, for brevity purposes, only the differences with respect to locking collar 200 are described below.

As shown, locking collar 200 has internal bore 202 which is defined by interior surface 204. Interior surface 204 includes threads 206, 208, 210, and 212, or sloping ramps. Threads 206, 208, 210, and 212 form a quad helix thread pattern extending circumferentially along interior surface 204 within internal bore 202. In that regard, threads 206 and 208 form a pair of opposing threads that are sloped in opposing directions with respect to each other. Additionally, threads 210 and 212 form a pair of opposing threads that are sloped in opposing directions with respect to each other.

Additionally, threads 206 and 208 create a pair of opposing spaces 214 for receiving projections 120 of female tubing fitting 102. Furthermore, threads 210 and 212 create a pair of opposing spaces 216 for receiving projections 120 of female tubing fitting 102. Thus, retractable locking collar 200 has four spaces for receiving projections 120. Therefore, when projections 120 are placed in spaces 214 and/or 216 and locking collar 200 is rotated male tubing fitting 104 and female tubing fitting 102 are locked together. Accordingly, retractable locking collar 200 provides an alternative locking collar having additional spaces and threading relative to retractable locking collar 106.

Moreover, it is contemptible that female tubing fitting 102 can include more than the two projections 120 shown in FIG. 1 when using retractable locking collar 200. For example, in alternative embodiments the female tubing fitting 102 can included two pair of opposing projections 120. As such, there are projections 120 for each of the spaces 214 and 216.

Additionally, there is no implied limitation on the number of and/or configuration of projections 120 as long as the projections 120 align with and are sized to be positioned within the spaces of the retractable locking collar. Similarly, there is no implied limitation on the number of and/or configuration of the threading in the retractable locking collars disclosed herein as long as the space formed by the threading is compatible with a given female tubing fitting.

While the present disclosure has been illustrated by the above description of embodiments, and while the embodiments have been described in some detail, it is not the intention of the applicants to restrict or in any way limit the scope of the present disclosure to such detail. Additional advantages and modifications will readily appear to those skilled in the art. Therefore, the present disclosure in its broader aspects is not limited to the specific details, representative apparatus and methods, and illustrative examples shown and described. Accordingly, departures may be made from such details without departing from the spirit or scope of the applicant's general or inventive concept.

We claim:

1. A retractable luer lock system comprising:
a male tubing fitting extending along a longitudinal axis and having a first internal bore and an end portion including a male plug, wherein the male tubing fitting comprises a plurality of flanges at the distal end thereof;
a female tubing fitting having a second internal bore configured to receive the male plug; and
a collar disposed about the male tubing fitting and positioned to slide freely along the longitudinal axis from a first position to a second position, wherein in the first position the male and female tubing fittings are unlocked with respect to each other such that the male plug is removably insertable into the second internal bore of the female tubing fitting and in the second position the male and female fittings are locked with respect to each other such that the male plug is prevented from being removed from the second internal bore of the female tubing fitting;
wherein the collar includes an elastically deformable portion that deforms in order to slidably position the collar along the longitudinal axis from the first position to the second position,
wherein the male tubing fitting includes a retention member that selectively retains the collar in the first position;
wherein the elastically deformable portion includes a tapered lip, the tapered lip interfacing with the retention member to selectively retain the collar in the first position;
wherein the elastically deformable portion includes slits that interrupt the tapered lip thereby allowing the tapered lip to deform outwardly from the longitudinal axis to slide the collar beyond the selective retainment of the retention member; and
wherein an entire internal diameter of the tapered lip prevents the collar from moving over the plurality of flanges.

2. The system of claim 1, wherein the collar internal diameter defines a third internal bore such that the male tubing fitting is disposed through the third internal bore, the third internal bore having a thread pattern that defines a space.

3. The system of claim 2, wherein the female tubing fitting has an exterior surface that includes a projection,
wherein the projection is disposed in the space when the collar is in the second position thereby sealingly engaging and locking the first internal bore of the male tubing fitting with the second internal bore of the female tubing fitting.

4. The system of claim 1, wherein the collar is rotatable about the longitudinal axis with respect to the male tubing fitting.

5. A retractable luer lock system comprising:
a male tubing fitting having an exterior surface and extending along a longitudinal axis and having a tapered end portion, the male tubing fitting including a first internal bore and a plurality of flanges at the distal end of the male tubing fitting;
a female tubing fitting having a second internal bore configured to receive the tapered end portion and an exterior surface including a projection; and
a collar disposed about the exterior surface of the male tubing fitting and rotatable about the longitudinal axis with respect to the male tubing fitting, the collar includes a threaded internal bore having an interior surface that includes a thread pattern defining a space configured to removably receive the projection of the female tubing fitting,
wherein rotation of the collar about the longitudinal axis relative to the male tubing fitting when the projection is positioned within the space sealingly engages and locks the first internal bore of the male tubing fitting with the second internal bore of the female tubing fitting;
wherein the collar includes an elastically deformable portion that deforms in order to slidably position the collar along the longitudinal axis from a first position to a second position, wherein in the first position the male and female tubing fittings are unlocked with respect to each other such that the male tapered end portion is removably insertable into the second internal bore of the female tubing fitting and in the second position the male and female fittings are locked with respect to each other such that the male tapered end portion is prevented from being removed from the second internal bore of the female tubing fitting,
wherein the male tubing fitting includes a proximal retention member that selectively retains the collar in the first position;
wherein the elastically deformable portion includes a tapered lip, the tapered lip interfacing with the proximal retention member to selectively retain the collar in the first position;
wherein the elastically deformable portion includes slits that interrupt the tapered lip thereby allowing the tapered lip to deform outwardly from the longitudinal axis to slide the collar beyond the selective retainment of the proximal retention member; and
wherein an entire internal diameter of the tapered lip prevents the collar from moving over the plurality of flanges.

6. The system of claim 5, wherein the exterior surface of the male tubing fitting further includes a distal retention member, the distal retention member selectively retaining the collar in the second position.

7. The system of claim 6, wherein the elastically deformable portion deforms in order to position the collar proximal the selective retainment of the distal retention member.

8. The system of claim 7, wherein the proximal retention member is a first nub extending around a perimeter of the exterior surface of the male tubing fitting and the distal retention member is a second nub extending around the perimeter of the exterior surface of the male tubing fitting.

9. The system of claim 5, wherein the thread pattern includes a pair of opposing ramps disposed circumferentially on the interior surface of the threaded internal bore, the pair of opposing ramps defining the space.

10. A retractable luer lock system comprising:
a male tubing fitting having an exterior surface extending along a longitudinal axis and including a proximal retention member, the male tubing fitting further including a first internal bore, a tapered end portion, and a plurality of flanges at the distal end of the male tubing fitting;
a female tubing fitting having a second internal bore configured to receive the tapered end portion; and a collar disposed about the exterior surface of the male tubing fitting and selectively retained by the proximal retention member at a first position along the longitudinal axis, wherein the collar includes an elastically deformable portion that deforms in order to position the collar beyond the selective retainment of the proximal retention member to a second position along the longitudinal axis, wherein in the first position the male and female tubing fittings are unlocked with respect to each other such that the tapered end portion is removably insertable into the second internal bore of the female tubing fitting and in the second position the male and female fittings are locked with respect to each other such that the tapered end portion is prevented from being removed from the second internal bore of the female tubing fitting;

wherein the elastically deformable portion includes a tapered lip, the tapered lip interfacing with the proximal retention member to selectively retain the collar in the first position;

wherein the elastically deformable portion includes slits that interrupt the tapered lip thereby allowing the tapered lip to deform outwardly from the longitudinal axis to slide the collar beyond the selective retainment of the proximal retention member; and wherein an entire internal diameter of the tapered lip prevents the collar from moving over the plurality of flanges.

11. The system of claim 10, wherein the female tubing fitting has an exterior surface including a projection, wherein the collar has an internal bore having an interior surface including a pair of opposing threads extending circumferentially about the interior surface, the pair of opposing threads creating a space for removably receiving the projection of the female tubing fitting, wherein rotation of the collar about the longitudinal axis relative to the male tubing fitting when the projection is positioned within the space sealingly engages and locks the first internal bore of the male tubing fitting with the second internal bore of the female tubing fitting.

12. The system of claim 10, wherein the male tubing fitting includes a second retention member adjacent the tapered end portion such that the collar is selectively retained in the second position.

* * * * *